Figure 3:
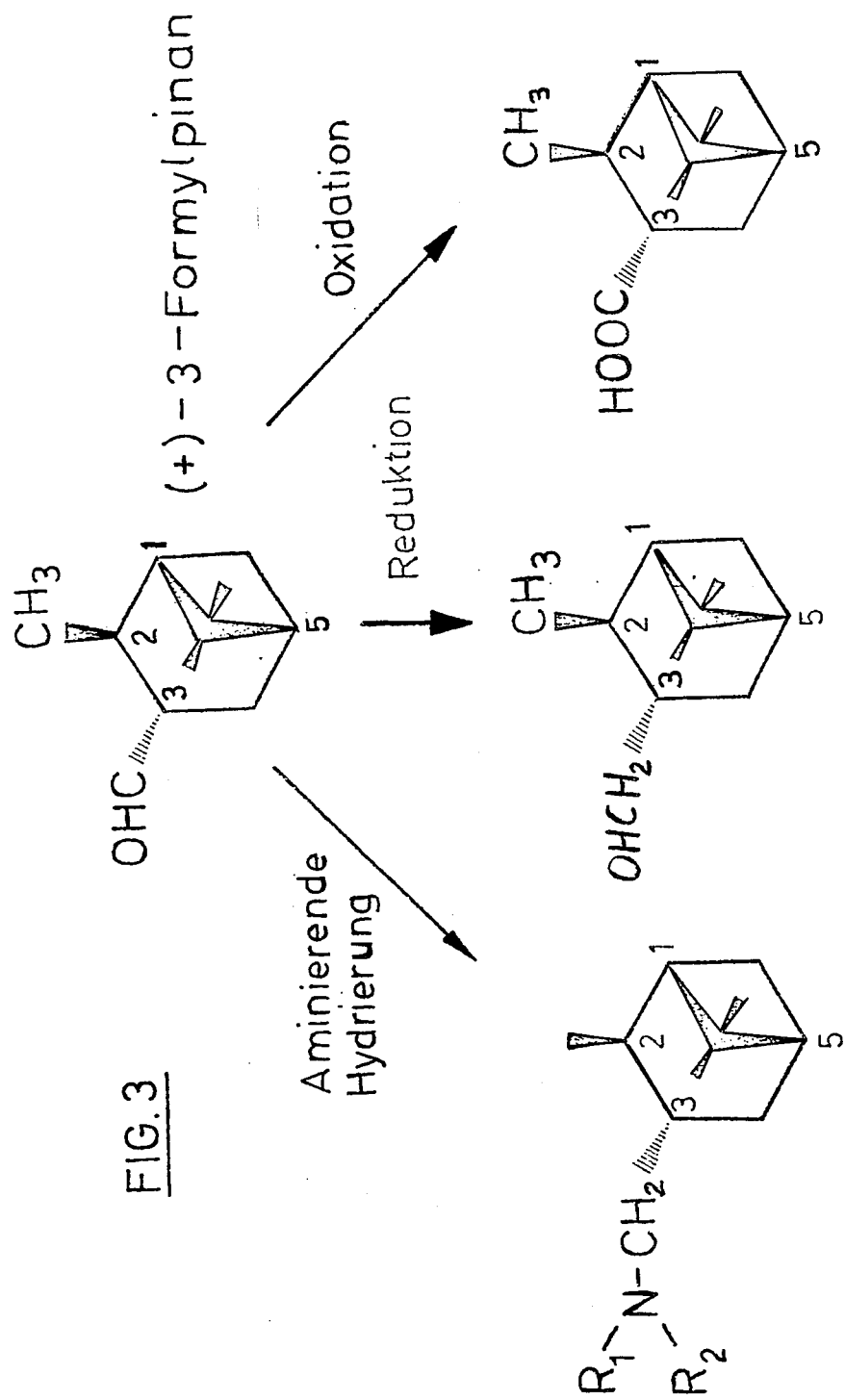

United States Patent [19]

Hoffmann et al.

[11] 4,081,477

[45] Mar. 28, 1978

[54] PINANE DERIVATIVES

[75] Inventors: Werner Hoffmann, Neuhofen; Walter Himmele, Walldorf; Joachim Paust, Neuhofen; Karl Von Fraunberg, Bad Duerkheim; Hardo Siegel, Ludwigshafen; Sigberg Pfohl, Speyer, all of Germany

[73] Assignee: BASF Aktiengesellschaft, Rheinland,Pfalz, Germany

[21] Appl. No.: 544,306

[22] Filed: Jan. 27, 1975

[30] Foreign Application Priority Data

Jan. 30, 1974 Germany .............................. 2404306

[51] Int. Cl.$^2$ ........................................... C07C 87/40
[52] U.S. Cl. ................................ 260/563 P; 560/117; 260/293.56; 260/570.8 R; 260/326.8; 260/570.9; 260/577; 260/514 G; 260/544 E; 260/557 B; 260/586 G; 260/617 F
[58] Field of Search ................................... 260/563 R

[56] References Cited

U.S. PATENT DOCUMENTS

| 3,584,045 | 6/1971 | Feldman | 260/563 R |
| 3,773,802 | 11/1973 | Zschocke et al. | 260/563 R X |
| 3,843,499 | 10/1974 | Giese et al. | 260/563 R X |
| 3,845,048 | 10/1974 | Baronnet | 260/563 R X |

Primary Examiner—Paul F. Shaver
Attorney, Agent, or Firm—Keil, Thompson & Shurtleff

[57] ABSTRACT

Pinanes substituted by a group X in the 3-position which group is formyl, or its alkyl-acetals or alkyl-hemiacetals, carboxylic acid, carboxylic acid chloride, carboxylic acid amide, hydroxymethyl or aminomethyl substituted in a specific manner at the nitrogen, the optical isomers of these compounds and a process for their manufacture by hydroformylation of α-pinene in the presence of rhodium catalysts, and conversion of the 3-formylpinane first produced into the above derivatives by conventional methods.

3 Claims, 3 Drawing Figures

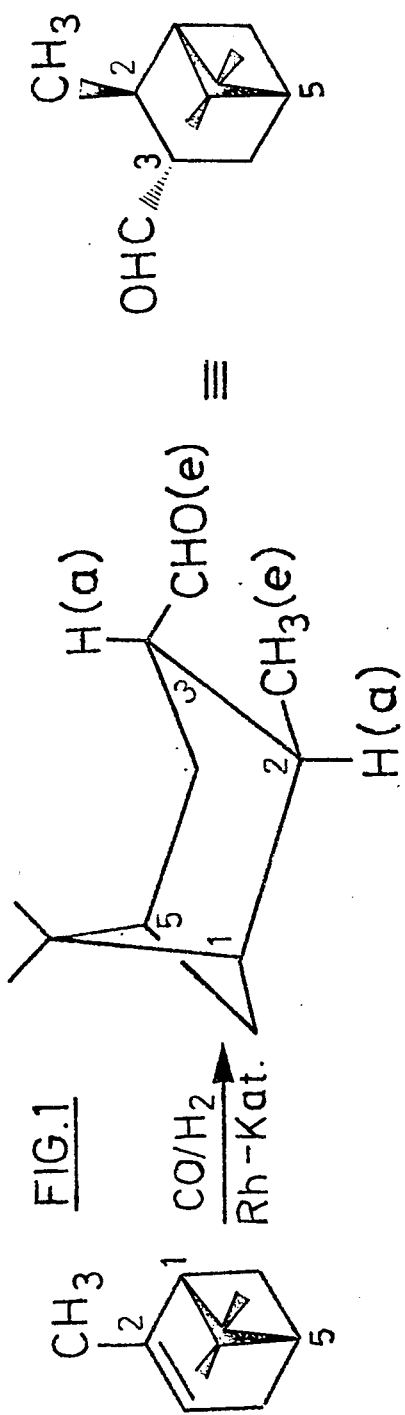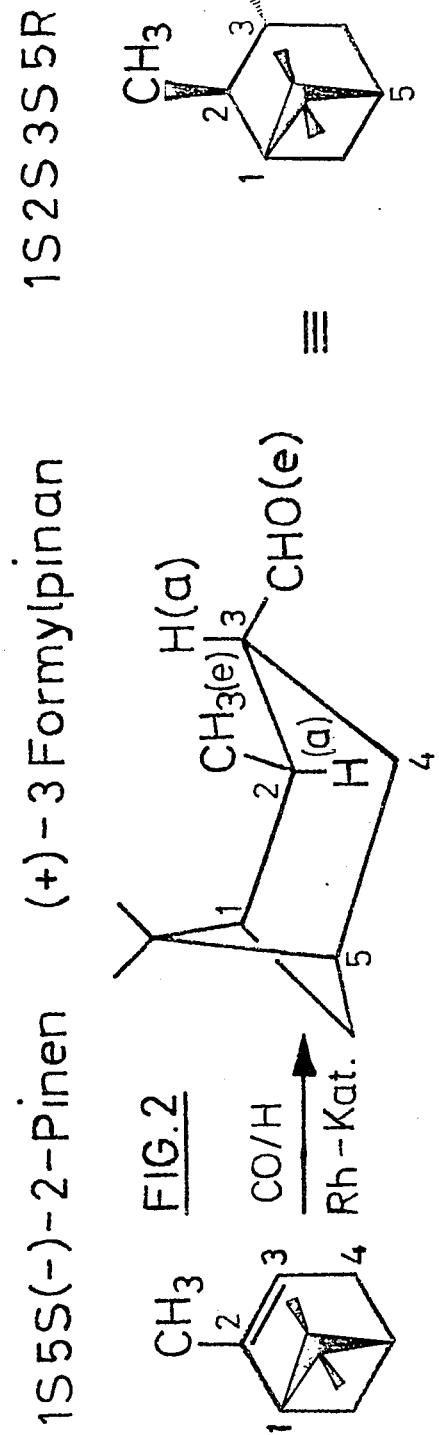

PINANE DERIVATIVES

This application discloses and claims subject matter described in German Patent Application No. P 24 04 306.9, filed Jan. 30, 1974, which is incorporated herein by reference.

The present invention relates to pinane derivatives of the general formula I

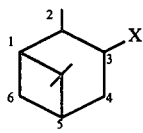

wherein X is (a) formyl or its acetals or hemiacetals with alkanols or alkanediols of up to 5 carbon atoms, (b) carboxyl, (c) a group of the formula —(CO)Y, in which Y is chlorine, —$NH_2$ or alkoxy of up to 4 carbon atoms, (d) hydroxymethyl or (e) a group of the formula —$CH_2$—$N(R^1)R^2$ in which $R^1$ and $R^2$ are hydrogen, alkyl of 1 to 12 carbon atoms, cycloalkyl of 5 to 8 carbon atoms, aralkyl of 7 to 10 carbon atoms or phenyl, or $R^1$ and $R^2$ together with the nitrogen can be a fivemembered or six-membered ring, and wherein the carbon atoms in positions 1, 3 and 5 are to be viewed as being in the plane of the paper, the 1,5-endo bridge and the 2-methyl group above the plane of the paper and the group X below the plane of the paper.

The invention further relates to the optical isomers

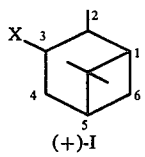 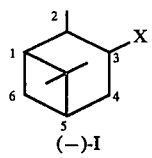

(+)-I       (−)-I and to processes for the manufacture of (I) and its optically pure isomers.

It is known that the antipodes of optical isomers frequently show different, or graded, physiological effects.

E.g., some of these pairs of isomers differ in pharmacological properties. This applies equally to naturally occurring materials and to synthetic compounds. Categories of compounds important from this point of view are, e.g., aminoacids and the oligopeptides and peptidehormones derived therefrom, particularly steriods, antibiotics and prostaglandins. Examples of compounds of commercial importance which are in the main marketed in an optically active form are lysine, α-methyldopa, l-dopa, calcium pantothenate, vitamin $B_2$, menthol, chloramphenicol and ethambutol.

The previously best-known and industrially most commonly used method of manufacturing compounds in their optically pure form is to resolve racemates. Unfortunately, the naturally occurring chiral compounds which can be used for this purpose are not obtainable in sufficient amounts and are frequently also physiologically usafe, as in the case of the alkaloids quinine, strychnine, brucine, cinchonine or quinidine. A further disadvantage is that the optically active naturally occurring compounds, e.g. tartaric acid, only occur in nature in one optically active form and therefore only one of the enantiomers can be isolated if they are used for the industrial resolution of racemates.

Numerous attempts have therefore already been made to modify optically active naturally occurring compounds by chemical methods and to use these derivatives for the resolution of racemates. Examples which may be mentioned are dibenzoyltartaric acid or diacetyltartaric acid obtained from tartaric acid, camphorsulfonic acid or bromocamphorsulfonic acid obtained from camphor, pyroglutamic acid obtained from glutamic acid, menthoxyacetic acid and menthylamine obtained from menthol and dehydroabietylamine obtained from abietic acid. However, even this extended range is frequently insufficient to permit economical resolution of racemates. This applies all the more since some of the above compounds are also difficult to produce and have a limited range of application.

It is an object of the present invention to provide more readily obtainable optically active compounds which because of the ease of modification of their functional groups have a broad range of applications in the resolution of racemates.

We have found that pinane derivatives of the general formula I

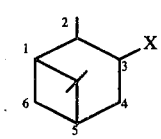

wherein X is (a) formyl or its acetals or hemiacetals with alkanols or alkanediols of up to 5 carbon atoms, (b) carboxyl, (c) a group of the formula —(CO)Y, in which Y is chlorine, —$NH_2$ or alkoxy of up to 4 carbon atoms, (d) hydroxymethyl or (e) a group of the formula —$CH_2$—$N(R^1)R^2$ in which $R^1$ and $R^2$ are hydrogen, alkyl of 1 to 12 carbon atoms, cycloalkyl of 5 to 8 carbon atoms, aralkyl of 7 to 10 carbon atoms or phenyl, or $R^1$ and $R^2$ together with the nitrogen can be a five-membered or six-membered ring, and wherein the carbon atoms in positions 1, 3 and 5 are to be viewed as being in the plane of the paper, the 1,5-endo bridge and the 2-methyl group above the plane of the paper and the group X below the plane of the paper, are a valuable new category of compounds of which the optical antipodes (+)−I and (−)−I are outstandingly suitable for the resolution of racemates.

Further, we have found that the compounds I are obtained by a remarkable reaction wherein α-pinene

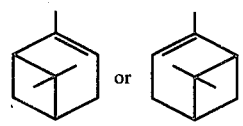

or mixtures of the two enantiomers are reacted with carbon monoxide and hydrogen at temperatures of from 65° to 140° C under superatmospheric pressure in the presence of rhodium carbonyl complexes to give 3-formylpinane (I,X = —CHO) and this compound is optionally converted by conventional methods into the other compounds I in which X can have the meanings defined above.

This process is noteworthy inasmuch as the formally similar hydroformylation of α-pinene in the presence of cobalt catalysts does not give 3-formylpinane but other reaction products, some of which are difficult to identify ("Ind. and Eng. Product Research and Development", 4, 1965, p. 283 et seq. and "Chimie et Industrie", 63, 1950, Special Issue, p. 468).

The process according to the invention has the unexpected advantage that the α-pinene skeleton is almost entirely preserved. E.g., if pure (+)—α-pinene is used as the starting material, (−)-3-formylpinane is obtained almost exclusively, apart from the customary by-products. The same is true of the reaction of pure (−)-α-pinene, which gives practically pure (+)-3-formylpinane. Whilst from the chemical point of view it is most advantageous to use the optically pure α-pinenes as starting materials, it is frequently more economical to use commercially available α-pinene which contains from 80 to 85% of one antipode, depending on its origin.

When converting the 3-formylpinane to the derivatives Ib to Ie, the pinane configuration once again virtually remains unchanged, contrary to expectation. Most of these derivatives, above all 3-aminomethylpinane and 3-carboxypinane, can then easily be purified further by fractional crystallization of their salts.

FIGS. 1 and 2 illustrate the steric relationships of the starting materials and products of the process, and FIG. 3 shows that even the derivatives of 3-formylpinanes can be obtained without racemization or partial rearrangement in the pinane skeleton. The systematic nomenclature shown in the figures, e.g. "1S5S(−)-2-pinene", corresponds to the nomenclature laid down by Ernest L. Eliel, "Stereochemie der Kohlenstoffverbindungen", Verlag Chemie GmbH, 1966.

The hydroformylation is carried out with carbon monoxide and hydrogen, as a rule in a volume ratio of from 1:0.5 to 1:2. A volume ratio of from 1:0.8 to 1:1.25 has proved particularly suitable. As in conventional processes, the said gas mixture of carbon monoxide and hydrogen is employed at least in stoichiometric amounts, based on α-pinene, but preferably in excess, e.g. up to 200 mole percent.

The pressure used is advantageously from 50 to 1,200 atmospheres, in particular from 100 to 700 atmospheres. The reaction is carried out at from 65° to 140° C and particularly good results are obtained at from 80° to 120° C, especially at from 90° to 110° C.

Though the nature of the catalytic rhodium carbonyl complexes is not known precisely, it is to be assumed that they are rhodium carbonyl or rhodium carbonyl hydride in which one or more carbonyl ligands can be replaced by equivalent ligands. It is therefore possible to start from previously produced rhodium carbonyl or to form the catalyst in situ under the reaction conditions, e.g. from rhodium chloride, rhodium oxide, rhodium chelates, rhodium salts with fatty acids and dimeric rhodium carbonyl chloride. It is also possible to use acyl complexes of rhodium or rhodium carbonyl complexes which are modified with amines or preferably with tertiary organic phosphines, advantageously with phosphines in which the substituents are alkyl radicals of up to 20 carbon atoms or phenyl radicals which can be substituted by alkyl or alkoxy groups of up to 4 carbon atoms. Rhodium-olefin complexes and rhodium-diolefin complexes have proved particularly suitable, especially those with 1,5-cyclooctadiene and 1,5-hexadiene.

It is advantageous to use the rhodium carbonyl complexes in amounts of from 5 to 5,000 ppm, especially of from 15 to 400 ppm, calculated as metal and based on 2-pinene. The amount of rhodium complex used depends on the rate at which the reaction is to take place and can be determined by a few experiments. OF course, since rhodium is expensive, the amount used will not be more than is necessary to ensure the success of the process.

The reaction can be carried out in the absence of solvents, in which case the products serve as the solvent. However, it is advantageous to use solvents such as saturated hydrocarbons of boiling point, e.g., from 40° to 160° C, e.g. pentane, isohexane, n-heptane, cyclohexane, cyclooctane, benzene, toluene or xylenes. Ethers such as tetrahydrofuran and dioxan, alkanols such as ethanol and methanol or diols such as glycol or propyleneglycol can also be used. The preferred solvents are hydrocarbons or ethers, and especially saturated hydrocarbons. The amount of solvent used is preferably from 50 to 200% by weight, based on pinene.

An advantageous method of obtaining the 3-formylpinane from the reaction mixture is to separate the distillable constituents by molecular distillation from the residue, containing catalyst, which can in turn be reused for the hydroformylation. It is advantageous to subject the distillate to fractional distillation, e.g. in a column with from 10 to 30 plates, using a reflux ratio of from 1:3 to 1:5, and preferably working under reduced pressure, e.g. at from 10 to 100 mm Hg.

The compounds Ib to Ie, as defined above, are obtainable from 3-formylpinane (Ia) by conventional methods.

Thus, 3-carboxypinane (Ib) is produced by oxidation of 3-formylpinane with molecular oxygen or air at elevated temperatures, advantageously at from 20° to 100° C and especially at from 25° to 60° C. The oxidation can be carried out in the absence of catalysts or in the presence of catalytic compounds which accelerate the oxidation, such as heavy metal salts, e.g. salts of copper, manganese or cobalt.

In another method, 3-carboxypinane is obtained by oxidation of 3-formylpinane with nitric acid, preferably concentrated nitric acid, in the presence of catalytic compounds such as vanadium pentoxide and copper compounds, e.g., copper sulfate. The temperatures used are advantageously from 10 to 40° C and especially from 20° to 30° C. However, the conversion of 3-formylpinane to 3-carboxypinane can also be carried out with other oxidizing agents, such as potassium permanganate or peroxides and per-acids.

The compounds Ic are obtained from 3-carboxypinane (Ib) by conventional methods of chlorination, amidation or esterification.

3-Hydroxymethylpinanes (Id) are obtained by reduction of 3-formylpinane, for example by catalytic reduction with hydrogen in the presence of conventional hydrogenation catalysts, especially metals of group VIII of the periodic table, e.g. cobalt catalysts or nickel catalysts which may contain activators such as copper, chromium or manganese. Such catalysts can be unsupported or can be supported on aluminum oxide, pumice or silica gel and contain, e.g., from 5 to 40 percent by weight of catalytically active metals. Other suitable catalysts are so-called Adkins catalysts, i.e. copper/chromium oxide catalysts, and noble metal catalysts, especially supported on aluminum oxide and charcoal. Platinum, palladium and ruthenium catalysts, and amongst these above all palladium catalysts, are especially preferred. The hydrogenation can be carried out under moderate pressure, e.g. of up to 20 atmospheres, especially when noble metal catalysts are used. However, when using cobalt and nickel catalysts in particular it is advisable to use higher pressure, of from 50 to 200 atmospheres. Advantageous hydrogenation temperatures are from 30° to 200° C; when noble metal catalysts are used, temperatures of from 10° to 40° C suffice whilst when cobalt catalysts and nickel catalysts are used higher temperatures, e.g. of from 90° to 180° C, are of advantage.

Other reducing agents, e.g. sodium borohydride or lithium aluminum hydride can be used instead of catalytic hydrogenation.

An advantageous method of obtaining 3-aminomethylpinanes (Ie) from 3-formylpinane is aminating hydrogenating, in which 3-formylpinane is reacted with ammonia or primary or secondary amines which are substituted by alkyl of 1 to 12, especially of 1 to 6, carbon atoms, cycloalkyl of 5 to 8, especially of 6 to 8, carbon atoms, aralkyl of 7 to 10 carbon atoms, especially benzyl, or phenyl. Other suitable amines are five-membered or six-membered heterocyclic amines such as pyrrolidine or piperidine. As a rule, the reaction is carried out in the presence of hydrogen at from 100° to 200° C and under pressures of from 50 to 200 atmospheres. The catalysts used are conventional hydrogenation catalysts, especially metals of group VIII of the periodic table, e.g. cobalt catalysts or nickel catalysts, which can contain up to 30 percent by weight of activators such as copper, chromium, manganese or zinc. Such catalysts are used either as unsupported catalysts, e.g. Raney nickel or Raney cobalt, or precipitated on carriers such as aluminum oxide, pumice, charcoal or silica gel. Advantageously, such supported catalysts contain from 5 to 40 percent by weight of the catalytically active metals.

3-Aminomethylpinane can also be prepared by the reaction of 3-formylpinane with amines to give Schiff's bases, followed by hydrogenation of these. Other suitable methods are the Leuckhart-Wallach aminating hydrogenation in which aldehydes are reacted with amines in the presence of formic acid. This method is applied particularly to the case of secondary amines.

The optically active 3-carboxypinanes and 3-aminomethylpinanes which can be used with particular advantage for the resolution of racemates can easily be obtained in an optically pure form by crystallization. An advantageous method is to convert 3-carboxypinanes into their salts with amines, e.g. alkylamines or aralkylamines, such as benzylamine, and to recrystallize the salts. The free 3-carboxypinanes can be obtained from the ammonium salts by conventional methods, e.g. by treatment with alkali metal hydroxide solutions, removal of the amines and acidification with mineral acids.

An advantageous method of purifying 3-aminomethylpinanes is to convert them into salts with strong mineral acids. e.g. hydrochloric acid or sulfuric acid. The preferred method of purification is to use salts with hydrochloric acid and recrystallize these. The aminomethylpinanes are obtained from the purified salts by conventional methods, e.g. by treatment with alkali metal hydroxide solutions and isolation of the liberated amine.

The compounds of the formula I can be used to resolve racemates into their enantiomers. Optically active 3-carboxypinanes, 3-hydroxymethylpinanes and 3-aminomethylpinanes are particularly suitable for this purpose. The optically active pinanes which contain a functional group in the 3-position are reacted with the racemates which are to be resolved, and the enantiomers are obtained by conventional methods, e.g. fractional crystallization. The compounds of the formula I extend the range of optically active compounds available for the resolution of racemates, since they are simple to produce on an industrial scale. This represents a not inconsiderably advance in the art.

EXAMPLE 1

(+)-3-Formylpinane 500 ml (428 g) of (−)-α-pinene of optical rotation $\alpha_D^{20} = -35.8°$ (pure, 1 dm) and 250 mg of dimeric rhodium 1,5-cyclooctadienyl chloride are introduced into a high pressure vessel of 1 liter capacity. After displacing the air with an equimolar mixture of carbon monoxide and hydrogen, the pressure is raised to 100 atmospheres and the reaction mixture is then heated to 110° C whilst maintaining a pressure of 650 atmospheres over 6 hours by injecting more of the above gas mixture. After cooling, and releasing the pressure, a reaction mixture which, according to gas chromatography, consists of 11 percent by weight of (−) -α-pinene, 61 per cent by weight of optically active 3-formylpinane and 26 percent by weight of by-products is obtained. The reaction mixture is distilled off the catalyst by molecular distillation under reduced pressure. The distillate is fractionally distilled in a column with 20 actual perforated plates, using a reflux ratio of 1:5. 285 g of (+)−3−formylpinane, $\alpha_D^{23} = -19.17°$ (pure), are obtained at from 103° to 104° C/18 mm Hg. The yield of (+)-3-formylpinane is 52% based on (−)-α-pinene.

EXAMPLE 2

(+)-3-Formylpinane 710 g of (−)-α-pinene and .500 mg of dimeric rhodium 1,5-cyclooctadienyl chloride are introduced into a tumbler autoclave of 3 liters capacity. The hydroformylation is carried out with an equimolar mixture of carbon monoxide and hydrogen, initially at 90° C and 270 atmospheres for 14 hours and then at 100° and 290 atmospheres for 6 hours. After cooling, and releasing the pressure, the reaction mixture is found, by gas chromatography, to contain 6 percent by weight by unconverted α -pinene, 64 percent by weight of (+)-3-formylpinane and about 30 percent by weight of higher-boiling by-products. The reaction mixture is separated from the residue, containing the catalyst, the molecular distillation. 735 g of distillate are obtained and are then fractionally distilled in a 20-plate column, as described in Example 1. 503 g of (+)-3-formylpinane boiling at from 110° to 112° C/19 mm Hg are obtained.

EXAMPLE 3

(+)-3-Formylpinane 50 g of (−)-α-pinene, 50 ml of toluene and 100 mg of dimeric rhodium 1,5-cyclooctadienyl chloride are introduced into a shaken autoclave of 220 ml capacity and are hydroformylated with an equimolar mixture of carbon monoxide and hydrogen. The gas taken up is equivalent to a pressure change of 10 atmospheres in the course of 10 hours at 70° C and 250 atmospheres gauge, 20 atmospheres in the course of a further 20 hours at 90° C and 270 atmospheres gauge, and 65 atmospheres in the course of a further 14 hours at 100° C and 300 atmospheres gauge. After cooling, and releasing the pressure, 89 g of reaction mixture are obtained, containing, according to gas chromatography, 59 percent by weight of unconverted pinene, 31 percent by weight of (+)-3-formylpinane and 27 percent by weight of higher-boiling isomers.

EXAMPLE 4

(+)-3-Formylpinane

The procedure followed is as in Example 1. 500 ml of (−)-α-pinene are hydroformylated, in the presence of 125 mg of rhodium 1,5-cyclooctadienyl chloride, with an equimolecular mixture of carbon monoxide and hydrogen, under a pressure of 650 atmospheres. The results shown in the table below are obtained at various temperatures, in each case with 6 hours reaction time:

| Temperature | Unconverted (−)-α-pinene [%] | (+)-3-formylpinane [%] |
|---|---|---|
| 80° C | 54.4 | 39.2 |
| 90° C | 27.4 | 63.3 |
| 100° C | 14.3 | 73.8 |
| 110° C | 9.7 | 70.9 |

EXAMPLE 5

(+)-3-Formylpinane 100 g of (−)-α-pinene and 100 mg of bis-triphenylphosphine-rhodium carbonyl chloride are hydroformylated with an equimolecular mixture of carbon monoxide and hydrogen for 12 hours at 80° C and 250 atmospheres, 12 hours at 90° C and 260 atmospheres, 12 hours at 100° C and 270 atmospheres and 12 hours at 110° C and 280 atmospheres. After cooling, and releasing the pressure, 100 g of reaction mixture are obtained; according to gas chromatography, the conversion is 21.4%. The mixture produced consists of 70% of (+)-3-formylpinane and 30% of other reaction products.

EXAMPLE 6

(−)-3-Formylpinane 250 ml of (+)-α-pinene, 250 ml of benzene and 125 mg of dimeric rhodium 1,5-cyclooctadienyl chloride are introduced into a high pressure vessel of 1 liter capacity and treated for 6 hours with an equimolecular mixture of carbon monoxide and hydrogen under a pressure of 600 atmospheres, at 110° C, the pressure being maintained constant by injecting more of the said gas mixture. The reaction mixture is worked up analogously to Example 1 and gives 123 g of (−)-3-formylpinane of boiling point 111° C/18 mm Hg, $a_D^{22} = 17.6°$ (pure).

EXAMPLE 7

(+)-3-Aminomethylpinane 300 g of ethanol and 50 g of Raney cobalt are introduced into a high pressure vessel of 2.5 liters capacity and the air is flushed out with nitrogen. The reaction mixture is then heated to 80° C and placed under a hydrogen pressure of 150 atmospheres. 200 g of (+)-3-formylpinane are introduced in the course of 6 hours and after a further 2 hours the reaction mixture is cooled and the pressure is released. 650 g of a mixture are obtained; its fractional distillation gives 106 g of (+)-3-aminomethylpinane boiling at from 110° to 111° C/20 mm Hg. 120 g of the 3-aminomethylpinane are dissolved in 1.3 l of pentane and dry hydrogen chloride is passed into the solution at from 0° to 5° C, whilst stirring. When free amine is no longer detectable the crystals produced are filtered off and dried. 142 g of (+)-3-aminomethylpinane hydrochloride of optical rotation $[α]_D^{23} = + 35.4°$ ( c = 1, methanol) are obtained.

118 g of (+)-3-aminomethylpinane hydrochloride, having an optical rotation of $[α]_D^{23} = + 35.4°$, are recrystallized from butyl acetate/ethanol. 85 g of (+)-3-aminomethylpinane hydrochloride of optical rotation $[α]_D^{23} = 40.5°$ are obtained. A further 29 g, of specific optical rotation $[α]_D^{23} = 17.3°$ are obtained from the mother liquor. The salt of optical rotation $[α]_D^{23} = + 40.5°$ is recrystallized a second time from butyl acetate/ethanol, giving 70 g of (+)-3-aminomethylpinane hydrochloride of specific optical rotation $[α]_D^{23} = + 44.3°$.

If 30 g of the (+)-3-aminomethylpinane hydrochloride of optical rotation $[α]_D^{23} = + 35.4°$ arerecrystallized three times from a mixture of ethyl acetate and methanol, a (+)-3-aminomethylpinane hydrochloride of specific optical rotation $[α]_D^{23} = + 44.7°$ are obtained.

EXAMPLE 8

(−)-3-Aminomethylpinane

The procedure described in Example 7 is applied analogously to (−)-3-formylpinane, and (−)-3-aminomethylpinane is obtained. 30 g of the latter are converted into (−)-3-aminomethylpinane hydrochloride by reaction with hydrogen chloride, analogously to Example 7. 34 g of (−)-3-aminomethylpinane hydrochloride of specific optical rotation $[α]_D^{23} = −33.8°$ (c = 1, $CH_3OH$) are obtained.

EXAMPLE 9

(+)-3-Methylaminomethylpinane

The procedure of Example 7 is followed, using methylamine instead of ammonia. The (+)-3-methylaminomethylpinane boils at from 118° to 120° C/18 mm Hg. (+)-3-Methylaminomethylpinane hydrochloride of optical rotation $[α]_D^{23} = + 30.8°$ is prepared by treatment with hydrogen chloride, analogously to Example 7. The (+)-3-methylaminomethylpinane hydrochloride obtained after two recrystallizations from a mixture of ethyl acetate and methanol has an optical rotation of $[α]_D^{23} = + 44.0°$ and melts at 240° C.

EXAMPLE 10

(+)-3-Pyrrolidinomethylpinane 33 g of (+)-3-formylpinane, 14 g of pyrrolidine and 70 g of formic acid are heated under reflux for 12 hours. Excess formic acid is then distilled off and the residue is boiled with 150 g of 25% strength aqueous potassium hydroxide solution. The amine separates out as the upper phase and is separated off and purified by fractional distillation. 31.8 g of (+)-3-pyrrolidinomethylpinane boiling at from 125° to 127° C/5 mm Hg are obtained.

(+)-3-Pyrrolidinomethylpinane is converted into (+)-3-pyrrolidinomethylpinane hydrochloride, of optical rotation $[α]_D^{23} = 41.3°$ ( c = 1, methanol), by treatment with hydrogen chloride, analogously to Example 7. The (+)-3-pyrrolidinomethylpinane hydrochloride obtained after three recyrstallizations, from a mixture of ethyl acetate and methanol, has a specific optical rotation of $[α]_D^{23} = + 49.4°$.

EXAMPLE 11

(+)-3-Piperidinomethylpinane

The procedure followed is as in Example 10 but piperidine is used instead of pyrrolidine. (+)-3-Piperidinomethylpinane boiling at from 138° to 140° C at 5 mm Hg is obtained. The hydrochloride, prepared analogously, has a optical rotation of $[\alpha]_D^{22} = +36.4°$. After three recrystallizations from a mixture of ethyl acetate and methanol, (+)-3-piperidinomethylpinane hydrochloride of specific optical rotation $[\alpha]_D^{23} = +47.8°$, and melting at 256° C, is obtained.

EXAMPLE 12

(+)-3-Dimethylaminomethylpinane

The procedure followed is analogous to that described in Example 7 except that dimethylamine is used instead of ammonia, and after analogous working up 3-dimethylaminomethylpinane boiling at from 93° to 95° C at 4 mm Hg is obtained. The hydrochloride, obtained analogously by reaction with hydrogen chloride, has a specific optical rotation of $[\alpha]_D^{22} = +42.6°$ (c = 1, methanol). After three recrystallizations from ethyl acetate/methanol, (+)-dimethylaminopinane hydrochloride having a specific optical rotation of $[\alpha]_D^{23} = 51.5°$ and melting at 239° C is obtained.

EXAMPLE 13

(+)-3-Carboxypinane 50 g of (+)-3-formalpinane are oxidized with air in an open vessel. Crystals separate out after 6 days and are filtered off and recrystallized from formic acid. 25 g of 3-carboxypinane, having an optical rotation of $[\alpha]_D^{25} = +21.8°$ (c = 1, methanol) and melting at 50° C, are obtained.

24 g of the (+)-3-carboxypinane are dissolved in petroleum ether and reacted with the stoichiometric amount of benzylamine. The benzylammonium salt of 3-carboxypinane precipitates and is filtered off; it melts at 128° C and its optical rotation is $[\alpha]_D^{22} = +13.1°$. After two recrystallizations from ethyl acetate, the specific optical rotation is $[\alpha]_D^{23} = +17.4°$. The salt thus obtained is then treated with aqueous hydrochloric acid and the hydrochloric acid solution is extracted with benzene. The benzene solution is dried and the benzene is then distilled off; the residue obtained is distilled. (+)-3-carboxypinane melting at 54° C and having a specific optical rotation of $[\alpha]_D^{24} = +23.5°$ (c = 1, CH$_3$OH) distils at from 120° to 121° C/0.6 mm Hg.

EXAMPLE 14

(−)-3-Carboxypinane 300 g of 65 percent strength by weight nitric acid, 350 mg of vanadium pentoxide and 350 mg of copper sulfate are introduced into a stirred flask and brought to 20° C. 140 g of (−)-3-formylpinane are then run in over 7 hours whilst maintaining the temperature at from 20° to 24° C by intensive cooling. Ice is then added to the reaction mixture and (−)-3-carboxypinane separates out as a viscous oil. 200 ml of toluene are added, the aqueous phase is separated off and the toluene is distilled from the organic phase in vacuo. The residue is stored for several days at 0° C and gives 79 g of crystals which are recrystallized from formic acid. (−)-3-Carboxyformylpinane, melting at from 48° to 50° C and having a specific optical rotation of $[\alpha]_D^{25} = +16.2°$ is thus obtained.

EXAMPLE 15

(+)-3-Hydroxymethylpinane 158 g of (+)-3-formylpinane, 500 ml of dioxane and 10 g of Raney cobalt are introduced into a high pressure vessel of 1 liter capacity. The mixture of hydrogenated for 4 hours at 40° C under a hydrogen pressure of 100 atmospheres and for 4 hours at 60° C under a pressure of 120 atmospheres. After cooling, and releasing the pressure, the catalyst is filtered off and the filtrate is subjected to fractional distillation. 101 g of (+)-3-hydroxymethylpinane boiling at 125° C at 10 mm Hg, and having an optical rotation of $[\alpha]_D^{22} = +29.4°$ (pure) are obtained.

The product is purified by esterifying it with 4-nitrobenzoic acid, recrystallizing the ester, and saponifying the purified ester. (+)-3-Hydroxymethylpinane of optical rotation $[\alpha]_D^{23} = +34.1°$ (pure) is obtained.

EXAMPLE 16

(+)-Pinane-3-carboxylic acid chloride 15 g of (+)-3-carboxypinane of optical rotation $[\alpha]_D^{25} = +20.2°$ (c = 1, CH$_3$OH) are boiled with excess thionyl chloride under reflux in the absence of moisture, until the evolution of gas has ceased. The excess thionylchloride is then distilled, followed by the acid chloride boiling at from 62° to 64° C/0.08 mm Hg and having an optical rotation of $[\alpha]_D^{24} = +28.1°$ (pure).

EXAMPLE 17

(+)-Pinane-3-carboxylic acid amide 2g of (+)-pinane-3-carboxylic acid chloride are mixed with concentrated aqueous ammonia solution; the corresponding carboxylic acid amide precipitates and is filtered off and dried. It melts at 131° C and has an optical rotation of $[\alpha]_D^{24} = +22.4°$ (c = 1, methanol).

EXAMPLE 18

(+)-Pinane-3-carboxylic acid methyl ester 4 g of (+)-pinane-3-carboxylic acid chloride are mixed with methanol and the solution is boiled under reflux in the presence of pyridine, then concentrated to a small volume, mixed with water and extracted with ether. Fractional distillation of the dried ether solution gives (+)-pinane-3-carboxylic acid methyl ester boiling at from 55 to 56° C/0.2 mm Hg and having an optical rotation of $[\alpha]_D^{24} = +18.9°$ (pure).

We claim:

1. Pinane derivatives of the formula I

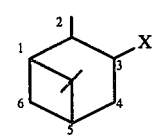

wherein X is a group of the formula —CH$_2$—N(R$^1$)R$^2$ in which R$^1$ and R$^2$ are hydrogen, alkyl of 1 to 12 carbon atoms, cycloalkyl of 5 to 8 carbon atoms, aralkyl of 7 to 10 carbon atoms or phenyl.

2. A pinane derivatives as set forth in claim 1 wherein R$^1$ and R$^2$ are hydrogen or alkyl of 1–12 carbon atoms.

3. A pinane derivative as set forth in claim 1 wherein R$^1$ and R$^2$ are hydrogen.

* * * * *